US007014844B2

(12) United States Patent
Mahalingam et al.

(10) Patent No.: US 7,014,844 B2
(45) Date of Patent: Mar. 21, 2006

(54) LIGHTENING COMPOSITIONS AND METHODS OF USE

(75) Inventors: Harish Mahalingam, Ledgewood, NJ (US); Brian Jones, Warwick, NY (US); Nicole McCain, Bronx, NY (US)

(73) Assignee: Avon Products, Inc., New York, NY (US)

( * ) Notice: Subject to any disclaimer, the term of this patent is extended or adjusted under 35 U.S.C. 154(b) by 0 days.

(21) Appl. No.: 10/319,781

(22) Filed: Dec. 13, 2002

(65) Prior Publication Data

US 2003/0157202 A1 Aug. 21, 2003

Related U.S. Application Data

(63) Continuation-in-part of application No. 10/034,186, filed on Dec. 28, 2001.

(51) Int. Cl.
*A61K 7/09* (2006.01)
*A61K 7/135* (2006.01)
*A61K 7/021* (2006.01)
*A61K 7/025* (2006.01)
*A61K 35/78* (2006.01)

(52) U.S. Cl. ............... 424/70.5; 424/401; 424/62; 424/63; 424/64; 424/725

(58) Field of Classification Search ........... 424/195.1, 424/725, 70.5, 401, 62, 63, 64
See application file for complete search history.

(56) References Cited

U.S. PATENT DOCUMENTS

| | | | | |
|---|---|---|---|---|
| 3,671,643 | A | * | 6/1972 | Kalopissis ............ 514/649 |
| 4,372,296 | A | * | 2/1983 | Fahim .................. 601/2 |
| 5,312,834 | A | * | 5/1994 | Yeo ..................... 514/560 |
| 5,980,904 | A | | 11/1999 | Leverett et al. ........ 424/195.1 |

FOREIGN PATENT DOCUMENTS

| | | |
|---|---|---|
| JP | 07025742 | 1/1995 |
| JP | 07187989 | 7/1995 |
| JP | 2001163759 | 6/2001 |
| JP | 2001181173 | 7/2001 |
| JP | 10265322 | 10/2001 |

OTHER PUBLICATIONS

Melasma (CHLOASMA); Jun. 1999, Redding Dermatology Medical Group, Inc. pp. 1-2; URL: <http://www.redding-dermatology.com/melasma.htm>.*
Chakraborty et al. "Effect of Arbutin melanogenic proteins in human melanocytes." Pigment Cell Res. 1998; 11: 206-212.
Chakroborty et al. "Melanogenic regulatory factors in coated vesicles from melanoma cells." J. Investigative Dermatology. vol. 93, No. 5, 616-620(1989).
Chakraborty et al. "Polymerization of 5,6-dihydroxyindole-2-carboxylic acid to melanin by the pmel 17/silver locus Protein." Eur. J. Biochem. 236, 180-188 (1996).
Orlow et al. "Synthesis and characterization of malanins from Dihydroxyindole-2-carboxylic acid and Dihydrozyindole." Pigment Cell Research. 5: 113-121 (1992).

* cited by examiner

*Primary Examiner*—Patricia Leith
(74) *Attorney, Agent, or Firm*—Ohlandt, Greeley, Ruggiero & Perle, L.L.P.

(57) ABSTRACT

There is provided a topical lightening composition having carboxylmethyl cysteamine as a melanin synthesis-regulating agent and a cosmetically acceptable vehicle. Also, there is provided a topical lightening composition having N, N, S (tris) carboxylmethyl cysteamine and a cosmetically acceptable vehicle. In addition, there is provided a topical lightening composition having carboxylmethyl cysteamine, preferably N, N, S (tris) carboxylmethyl cysteamine, and an additional lightening agent and a cosmetically acceptable vehicle. The compositions and methods of the invention are effective to lighten skin, hair, lips, and/or nails.

33 Claims, No Drawings

LIGHTENING COMPOSITIONS AND METHODS OF USE

RELATED APPLICATION

This application is a continuation-in-part of U.S. application Ser. No. 10/034,186, filed Dec. 28, 2001.

BACKGROUND OF THE INVENTION

1. Field of the Invention

The present invention relates to the lightening of the skin, hair, nails and/or lips. The present invention further relates to compositions and methods for lightening the skin, hair, nails and/or lips.

2. Description of the Related Art

By way of background, there is consumer interest in lightening and reducing uneven pigmentation in the skin. Common skin conditions treated include freckles, age spots, dark spots, hyperpigmentation, discoloration, melasma, cholasma, after-burn scar, nail stain, yellowing, and dark circles under the eye.

A variety of materials have been applied to the skin to lighten the skin. Such materials include hydroquinone, kojic acid, licorice and its derivatives, ascorbic acid and its derivatives, arbutin, bearberry, *Glycyrrhiza glabra* and its derivatives, *Chlorella vulgaris* extract, perilla extract, and coconut fruit extract. Perilla extract is disclosed as a whitening agent in U.S. Pat. No. 5,980,904 and Japanese Publications Nos. 07025742, 07187989, 10265322, 2001163759 and 2001181173. Coconut fruit extract is disclosed as a whitening agent in Japanese Patent No. 2896815 B2.

Skin and hair pigmentation is determined by the level of melanin present in the epidermis and hair fiber, respectively. For example, three different types of melanin are present in the epidermis: DHI-melanin, DHICA-melanin and pheomelanin. The different types of melanin vary in color or shade. DHI-melanin is the darkest and is blackish in color. DHICA-melanin is brownish in color. Pheomelanin is the lightest and is reddish in color.

Melanin, as described above, is synthesized in specialized organelles called melanosomes within pigment-producing cells (melanocytes). Melanocytes respond to stimuli and regulate melanin synthesis. Melanogenesis is regulated by a variety of environmental and hormonal factors. Melanocytes, which comprise less than 1% of the cells in the epidermis, respond to various signals with alterations in melanin synthesis. Melanin is deposited into organelles known as melanosomes that are transferred to the keratinocytes.

Most conventional topical lightening agents act by interfering with the action of tyrosinase, the enzyme that catalyzes the conversion of the amino acid tyrosine to DOPAquinone. Previously, it has not been known that hypopigmenting could be achieved by inhibiting enzymes "downstream" from tyrosinase in the melanin synthesis pathway by the use of the materials of the present invention. It has now been discovered that the use of the melanin synthesis regulating agent of the present invention inhibits DOPAchrome tautomerase and/or DHICA-polymerase and results in a composition with superior lightening, especially skin lightening.

It is desirable to have a topical composition that provides enhanced levels of lightening, bleaching, hypopigmenting, whitening and/or depigmenting (hereinafter referred to individually and collectively as "lightening" or "lighten"). It is also desirable to have a topical composition that has one or more lightening agents that acted to interfere with the conversion of DOPAchrome to DHI-melanin and DHICA-melanin. It is further desirable to have a topical composition that has one or more lightening agents that act to inhibit or impede the transfer (uptake) of melanin from the melanocytes to the keratinocytes. It is still further desirable to have methods for lightening the skin, hair, nails, and/or lips employing the compositions of the present invention.

SUMMARY OF THE INVENTION

It is an object of the present invention to provide a composition for lightening of the skin, hair, lips and/or nails.

It is another object of the present invention to provide a composition to alter/modify melanin synthesis in the skin, hair, lips and/or nails.

It is yet another object of the present invention to provide a composition to inhibit or impede the uptake of melanin by keratinocytes.

It is a further object of the present invention to provide a topical composition that lightens the skin by reducing melanin in hyperpigmented areas.

It is yet a further object of the present invention to provide methods for effecting the foregoing.

These and other objects and advantages of the present invention are provided by a topical lightening composition comprising carboxylmethyl cysteamine, more preferably N, N, S (tris) carboxylmethyl cysteamine, and a cosmetically acceptable vehicle. The composition may also have one or more other lightening materials. Most preferably, the composition is a topical lightening composition that has N, N, S (tris) carboxylmethyl cysteamine, one or more other lightening materials or combinations of lightening materials, and a cosmetically acceptable vehicle. There are also provided methods for lightening the skin, hair, lips, and/or nails comprising topically applying any one of these compositions.

DETAILED DESCRIPTION OF THE INVENTION

It has been found that there are topical lightening compositions that provide enhanced levels of performance heretofore not possible. It has also been found possible to enhance lightening by inhibiting enzymes other than tyrosinase, specifically DOPAchrome tautomerase (DCT) and/or 5,6-dihydroxyindole-2-carboxylic acid polymerase (DHICA-polymerase). It has also been found possible to enhance lightening by inhibiting the production of melanin and/or decreasing hypermelanocytic states.

In its broadest aspects, the present invention is not limited by any particular characterization of the mechanism of action of compositions to lighten skin, hair, nails and/or the lips, or the physiological, biochemical and/or chemical effects of topical lightening agents. However, the agents used in the present compositions and methods of the present invention lighten the skin by regulating melanin production, and altering, inhibiting, impeding or modifying the uptake of melanin in the skin, hair, lips, and/or nails, that result in lightening of the skin, hair, lips and/or nails.

One embodiment of the present invention uses a melanin synthesis-regulating agent alone, or in combination with a lightening agent and/or a melanin uptake-inhibiting agent. When the melanin synthesis-regulating agent is present in an amount effective to alter, impede, inhibit, or modify DCT and/or DHICA polymerase, a superior lightening composition can be attained.

It was heretofore unknown in the art that interference in this part of the melanin synthesis pathway with the compositions of the present invention could bring about lightening of the skin, hair, lips, and/or nails. A flow chart of the melanin synthesis pathway is as follows:

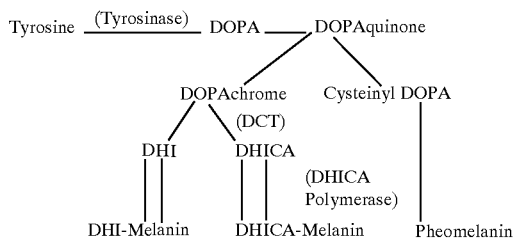

The present invention provides for the use of carboxylmethyl cystamine, preferably N, N, S (tris) carboxylmethyl cysteamine, as a melanin synthesis-regulating agent. The carboxylmethyl cystamine can be used either alone or in combination with one or more other lightening agents and/or one or more melanin uptake-inhibiting agents that alter the transfer and/or uptake of melanosomes by epidermal cells.

The present compositions that have carboxylmethyl cystamine, especially in an amount effective to regulate melanin synthesis, reduce melanin in hyperpigmented areas by decreasing dark pigment formation in melanocytes and shuttling or shifting the melanin synthesis path towards light melanin formation. Most of the prior art products that lighten human skin color are based on their ability to inhibit the activity of tyrosinase. One way to go from sun exposed skin "color" to sun protected skin "color" is to alter the melanin content to contain proportionately more lighter type of melanin. While not intending to be bound by the foregoing, it is believed that carboxymethyl cysteamine, especially N, N, S (tris) carboxylmethyl cysteamine, alters the levels and/or activity of DOPAchrome tautomerase that acts downstream from tyrosinase in the melanin synthesis pathway.

As stated above, the melanin synthesis-regulating agent, carboxylmethyl cysteamine, preferably N, N, S (tris) carboxylmethyl cysteamine, can be used in combination with one or more lightening agents. Such lightening agents include, but are not limited to, ascorbyl glucoside, vitamin C, retinol and/or retinol derivatives, water soluble licorice extracts, bearberry extract, *Rumex crispus* extract, milk protein, hydrolyzed milk protein, oleanolic acid, Perilla oil, placenta extract, *Saxifragia sarmentosa*, grape extract, Azadirachta indica A. Juss. Var., *Glycyrrhiza glabra* Linn, *Morinda citrifolia* Linn, *Naringi crenulata* (Roxb) Nicolson, *Ligusticum chiangxiong* Hort., *Asmuna japonica* Thumb., *Stellaria medica* (L.) cry., *Sedum sarmentosum* Bunge, *Ligusticum lucidum* Ait., *Ilex purpurea* Hassk, Emblica, hydroquinone, kojic acid, licorice and/or its derivatives, ascorbic acid and/or its derivatives, arbutin, bearberry, *Glycyrrhiza glabra* and/or its derivatives, *Chlorella vulgaris* extract, and any combinations thereof. Other lightening agents are disclosed in U.S. Pat. No. 5,980,904.

Other examples of lightening agents that can be used with the melanin synthesis-regulating agent of the present compositions are: coconut water, coconut milk, palm water, palm nut milk, pecan nut milk, almond nut milk, cashew nut milk, walnut nut milk, and concentrates of the foregoing, or any combinations of the foregoing. Coconut water is a preferred lightening agent. A freeze-dried concentrate of coconut water is most preferred. Coconut water or the concentrate thereof is believed to provide superior lightening efficacy compared to extracts, concentrates, or oils of other parts of the coconut and/or coconut tree, i.e. the fruit, milk, shell, seed, leaf, and bark.

As stated above, the melanin synthesis-regulating agent can be used in combination with one or more melanin uptake-inhibiting agents, and/or one or more lightening agents. The use of a melanin uptake-inhibiting agent functions to inhibit the transfer (uptake) of melanin from the melanocytes to the keratinocytes and further enhances the lightening efficacy of the present invention. Examples of such melanin uptake-inhibiting agents that can be used in the present compositions include, but are not limited to, extracts or oils derived from all or parts of the perilla plant, e.g. the leaf, seed, stem, and root; juniperic acid; tomato glycolipid, *Asmunda japonica* Thumb., *stenolama chusana* (L.) ching, *Ligusticum lucidum* Ait, and any combinations thereof. A preferred agent is extract of the perilla leaf.

The melanin synthesis-regulating agent, namely carboxylmethyl cysteamine, preferably N, N, S (tris) carboxylmethyl cysteamine, is present in compositions of the present invention in an amount about 0.001 percentage by weight (wt %) to about 20 wt %, based on the total weight of the composition. The melanin synthesis-regulating agent is present, more preferably, in an amount about 0.01 wt % to about 10 wt %, and most preferably in an amount about 0.01 wt % to about 5 wt %, based on the total weight of the composition.

In the present compositions that have one or more lightening agents, the one or more lightening agents are present at a level sufficient to induce the desired effect of lightening. The amount will vary depending upon the type of agent and the nature and level of desired effect. However, the lightening agents are typically be present in an amount about 0.001 wt % to about 20 wt %, more preferably about 0.01 wt % to about 5 wt %, and most preferably about 0.1 wt % to about 2.5 wt %, based on the total weight of the composition.

In the present compositions that have one or more melanin uptake-inhibiting agents, the one or more melanin uptake-inhibiting agents are typically present in an amount about 0.001 wt % to about 20 wt %, more preferably about 0.01 wt % to about 10 wt %, and most preferably about 0.01 wt % to about 5 wt %, based on the total weight of the composition.

The compositions of the present invention preferably include at least one, more preferably at least two, most preferably at least three, of the following ingredients: aloe barbadensis or an extract thereof, hydrolyzed soy protein, n-glucosamine, gamma-aminobutyric acid, a competitive inhibitor of melanocyte stimulating hormone (MSH) (e.g. hexapeptide-2), clintonia borealis (bluebeard lily) or an extract thereof, sanguisorba officinalis (burnet), a glutathione reductase inhbitor (e.g. wheat germ) or extracts thereof.

The compositions of the present invention can be used to effectively lighten skin, hair, lips and nails by topically applying the composition having an effective amount of carboxylmethyl cysteamine, preferably N, N, S (tris) carboxylmethyl cysteamine, and optionally one or more lightening agents and/or one or more melanin uptake-inhibiting agents. To lighten the color or shade of hair, the present compositions should preferably be rubbed onto/into the scalp so that the composition can penetrate into the hair follicles or root shafts and be absorbed into the hair during the melanin production process.

The topical compositions of the present invention can be applied to even/optimize skin discoloration, treat a variety of skin conditions, including: freckles; age spots; dark spots; hyperpigmentation; post-inflammatory hyperpigmentation (e.g. post-acne hyperpigmentation); discoloration; melasma; cholasma; after-burn scars; bleached/discolored hair located on the face, scalp, legs or other body areas; bleached nail stains; bleached hyperpigmented skin, hair and nails; yellowing; and dark circles under the eyes.

The present compositions may include any vehicle known in the art. Suitable vehicles include, but are not limited to, water; one or more vegetable oils; esters such as octyl palmitate, isopropyl myristate and isopropyl palmitate; ethers such as dicapryl ether and dimethyl isosorbide; alcohols such as ethanol and isopropanol; fatty alcohols such as cetyl alcohol, stearyl alcohol and behenyl alcohol; isoparaffins such as isooctane, isododecane and isohexadecane; silicone oils such as dimethicones and polysiloxanes; hydrocarbon oils such as mineral oil, petrolatum, isoeicosane and polyisobutene; polyols such as propylene glycol, glycerin, butylene glycol, pentylene glycol and hexylene glycol; or any combinations thereof.

The present compositions may include one or more of the following ingredients: anesthetic, anti-allergenic, antifungal, antimicrobial, anti-inflammatory, antiseptic, chelating agent, colorant, emollient, exfollient, film former, fragrance, humectant, insect repellent, lubricant, moisturizer, pharmaceutical agent, preservative, skin protectant, skin penetration enhancer, stabilizer, surfactant, thickener, viscosity modifier, vitamin, or any combinations thereof.

The compositions can be made into any suitable product form. Such product forms include, but are not limited to, a cream, a lotion, an ointment, a gel, a foam, a pomade, an aerosol spray, a pump spray, a stick, a towelette, or a patch.

Accordingly, the present invention is further illustrated by the following Examples that are intended for illustration and not for limitation of the scope thereof.

EXAMPLE 1

Reconstructed Pigmented Epidermal Tissue Assay

A composition containing 0.1 wt % N, N, S (tris) carboxylmethyl cysteamine was tested in a Reconstructed Pigmented Epidermal Tissue Assay. Reconstituted Human Epidermis (tissue) consisting of keratinocytes and Type IV (Fitzpatrick scale) melanocytes (Skin Ethic, France) were grown in maintenance medium obtained from the tissue supplier. This model consists of melanocytes and keratinocytes and the pigmentation of the skin-equivalent is due to melanin. The tissue remained viable through the course of the experimental treatment and actively synthesized and transferred melanin. The skin equivalents were treated for 14 days with the active materials of the present invention and a measure of melanin was obtained by measuring absorbance of the tissue at 490 nm. All studies were conducted in 6-well tissue culture dishes (Falcon), at 37° C. and 5% $CO_2$. All test articles were dissolved in medium. Tissues were fed 1 ml of medium with the active material or medium alone was used as the control. Tissues were exposed to test article or control medium for 14 days with re-feeding every other day. After 14 days the tissues were transferred to a 24-well tissue culture dish (Falcon), and pigmentation was assessed using a Packard microplate reader at 490 nm. Melanin absorbs at 490 nm. A control baseline reading had been taken on day 2 after the models had equilibrated and used as a baseline tissue pigmentation value. The baseline reading was subtracted from the final readings to eliminate inherent absorbance by the tissue. Percent pigmentation change=100×(OD sample−OD neg. control)/OD neg. control.

Results of this assay demonstrated that 0.1 wt % N, N, S (tris) carboxylmethyl cysteamine reduced reconstructed epidermal tissue (i.e., pigmentation) by about 40% in comparison to control tissue.

EXAMPLE 2

Tyrosinase, DOPAchrome Tautoamerase and DHICA Polymerase Assays

The effect of 0.05 wt % N, N, S (tris) carboxylmethyl cysteamine on tyrosinase, DOPAchrome tautomerase and DHICA polymerase activity was evaluated.

A tyrosinase assay was performed according to the method outlined in Chakraborty et al., 1989, Melanogenic regulatory factors in coated vesicles from melanoma cells, J. Invest. Dermatol. 93: 616–620. Specifically, mouse melanoma cells were dissolved with the addition of 0.1 M sodium phosphate buffer, pH 6.8, containing Triton X-100 (1% vol/vol), at a ratio of 1-5×106 cells/ml. After 10 minutes on ice, the extracts were centrifuged at 4° C. (10,000 g, for 10 minutes) and the supernatant fractions were assayed for tyrosinase. Tyrosinase was assayed spectrophotometrically by adding up to 0.1 ml cell extract to 0.2 ml of a solution of freshly prepared DOPA (~0.5 mg/ml), in a total volume of 0.5 ml of 0.1 M sodium phosphate buffer, pH 6.8. Reactions were carried out at 37° C. in plastic cuvettes, and the appearance of absorption at 475 nm was followed. It was demonstrated that 0.05 wt % N, N, S (tris) carboxylmethyl cysteamine provided an average decrease in tyrosinase conversion of 36% as compared to the control.

DOPAchrome tautomerase (DCT) activity was assayed according to the method disclosed in Chakraborty et al., 1998, Effect of arbutin on melanogenic proteins in human melanocytes, Pigment Cell Res. 11: 206–212. Specifically, ice-cold DOPA (0.5 mg per ml of 0.1 M sodium phosphate buffer, pH 6.8) was mixed with $Ag_2O$ (30 mg $Ag_2O$: 1 mg DOPA) for about 1 minute and filtered through a 0.22 $\mu m$ Millipore filter. DCT was assayed spectrophotometrically by adding up to 0.1 ml cell extract to 0.5 ml of a solution of freshly prepared DOPAchrome (~0.5 mg/ml). Reactions were carried out at room temperature in plastic cuvettes, and the disappearance of absorption at 475 nm was followed. Phenylthiourea (1 mM) was added to the reaction mixture, because the presence of tyrosinase in the cell extract can interfere with the assay. The percentage conversion of DOPAchrome was calculated per mg of protein extract and normalized against the control. It was demonstrated that 0.05 wt % N, N, S (tris) carboxylmethyl cysteamine provided an average decrease in DOPAchrome conversion of 65% as compared to the control.

A DHICA polymerase assay was performed according to the method disclosed in Chakraborty et al., 1996, Polymerization of 5, 6-dihydroxyindole-2-Carboxylic acid to melanin by the pmel17/silver locus protein, Eur. J. Biochem. 236: 180–188. Specifically, the cell extract (0.5 ml, 150–200 $\mu g$ protein) was passed through a wheat germ agglutinin column (1 ml bed volume) equilibrated with lysis buffer. The bound material was eluted with 0.5 ml 1M N-acetyl glucosamine, which contains crude DHICA polymerization factor and other melanogenic proteins. A reaction mixture of 0.5 ml containing either the enzyme preparation to be measured (20 $\mu g$ protein from wheat germ agglutinin eluates) or the appropriate buffer blank, DHICA (0.5 mM), and 100 mM sodium phosphate buffer, pH 7.0. Phenylthiourea was also included to inhibit endogenous tyrosinase activity in the preparation.

Spectrophotomeric reading of the absorbance of the reaction mixture was taken at T=0 and T=4 hours time points at 400 nm. DHICA-melanin, but not DHICA itself, has been shown to absorb light at these wavelengths (Orlow et al., 1992, Synthesis and characterization of melanins from dihydroxyindole-2-carboxylic acid and dihydroxyndole, Pigment Cell Res. 5: 113–121). An increase in absorbance over that seen in blank tubes was defined as specific DHICA polymerization factor activity. It was demonstrated that 0.05 wt % N, N, S (tris) carboxylmethyl cysteamine provided an average decrease in DHICA Polymerase conversion of 58% compared to the control.

These results show that 0.05 wt % N, N, S (tris) carboxymethyl cysteamine decreases DOPAchrome tautomerase activity, as well as DHICA polymerase activity.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A topical lightening composition, comprising:
   a) N, N, S (tris) carboxylmethyl cysteamine in an amount effective to regulate melanin synthesis; and
   b) a cosmetically acceptable vehicle.

2. The composition of claim 1, wherein said N, N, S (tris) carboxylmethyl cysteamine is in an amount effective to inhibit at least one of the following enzymes: tyrosinase, DOPAchrome tautomerase, and DHICA polymerase.

3. The composition of claim 1, wherein said N, N, S (tris) carboxylmethyl cysteamine is present in an amount about 0.001 wt % to about 20 wt % based on the total weight of the composition.

4. The composition of claim 1, wherein said carboxymethyl cysteamine is present in an amount about 0.01 wt % to about 10 wt % based on the total weight of the composition.

5. The composition of claim 1, wherein said carboxymethyl cysteamine is present in an amount about 0.01 wt % to about 5 wt % based on the total weight of the composition.

6. The composition of claim 1, wherein said N, N, S (tris) carboxylmethyl cysteamine is present in an amount effective to inhibit the transfer of melanin from melanocytes to keratinocytes.

7. The composition of claim 1, further comprising one or more lightening agents.

8. The composition of claim 7, wherein said one or more lightening agents are selected from the group consisting of ascorbyl glucoside, vitamin C, retinol and/or retinol derivatives, water soluble licorice extracts, bearberry extract, *Rumex crispus* extract, milk protein, hydrolyzed milk protein, oleanolic acid, Perilla oil, placenta extract, *Saxifragia sarmentosa*, grape extract, *Aradirachta indica* A. Juss. Var., *Glycyrrhiza glabra* Linn, *Morinda citrifolia* Linn, *Naringi crenulata* (Roxb) Nicolson, *Ligusticum chiangxiong* Hort., *Asmuna japonica* Thumb., *Stellaria medica* (L.) cry., *Sedum sarmentosum* Bunge, *Ligusticum lucidum* Ait., *Ilex purpurea* Hassk, *Emblica*, hydroquinone, kojic acid, licorice and/or its derivatives, ascorbic acid and/or its derivatives, arbutin, bearberry, *Glycyrrhiza glabra* and its derivatives, *Chlorella vulgaris* extract, coconut water, coconut milk, palm water, palm nut milk, pecan nut milk, almond nut milk, cashew nut milk, walnut nut milk, concentrates of the foregoing, and any combinations thereof.

9. The composition of claim 7, wherein said one or more lightening agents is present in an amount about 0.001 wt % to about 20 wt % based on the total weight of the composition.

10. The composition of claim 7, further comprising one or more melanin uptake-inhibiting agents.

11. The composition of claim 10, wherein said one or more melanin uptake-inhibiting agents are selected from the group consisting of extracts or oils derived from all or parts of the perilla plant, juniperic acid, tomato glycolipid, *Asmunda japonica* Thumb., *stenolama chusana* (L.) ching, *Ligusticum lucidum Ait*, and any combinations thereof.

12. The composition of claim 1, further comprising one or more melanin uptake-inhibiting agents.

13. The composition of claim 12, wherein said one or more melanin uptake-inhibiting agents are selected from the group consisting of extracts or oils derived from all or parts of the perilla plant, juniperic acid, tomato glycolipid, *Asmunda japonica* Thumb., *stenolama chusana* (L.) ching, *Ligusticum lucidum* Ait, and any combinations thereof.

14. The composition of claim 1, wherein the composition is in a product form selected from the group consisting of a cream, a lotion, an ointment, a gel, a foam, a pomade, an aerosol spray, a pump spray, a stick, a towelette, and a patch.

15. A method of lightening skin, hair, lips, and/or nails, comprising: applying topically to an area of the skin, scalp, hair, lips, or nails in need of lightening a composition having
   a) carboxylmethyl cysteamine in a lightening-effective amount; and
   b) a cosmetically acceptable vehicle wherein the composition is topically applied to treat at least one of the following conditions; freckles, age spots, hyperpigmentation, post-inflammatory hyperpigmentation, melasma, after-burn scar, nail stain, yellowing of skin and dark circles under eye.

16. The method of claim 15, wherein said carboxylmethyl cysteamine is N, N, S (tris) carboxylmethyl cysteamine.

17. The method of claim 16, wherein the composition further has one or more lightening agents.

18. The method of claim 17, wherein the one or more lightening agents one or more lightening agents is selected from the group consisting of ascorbyl glucoside, vitamin C, retinol and/or retinol derivatives, water soluble licorice extracts, bearberry extract, *Rumex crispus* extract, milk protein, hydrolyzed milk protein, oleanolic acid, Perilla oil, placenta extract, *Saxifragia sarmentosa*, grape extract, *Aradirachta indica* A. Juss. Var., *Glycyrrhiza glabra* Linn, *Morinda citrifolia* Linn, *Naringi crenulata* (Roxb) Nicolson, *Ligusticum chiangxiong* Hort., *Asmuna japonica* Thumb., *Stellaria medica* (L.) cry., *Sedum sarmentosum* Bunge, *Ligusticum lucidum* Ait., *Ilex purpurea* Hassk, *Emblica*, hydroquinone, kojic acid, licorice and/or its derivatives, ascorbic acid and/or its derivatives, arbutin, bearberry, *Glycyrrhiza glabra* and its derivatives, *Chlorella vulgaris* extract, coconut water, coconut milk, palm water, palm nut milk, pecan nut milk, almond nut milk, cashew nut milk, walnut nut milk, concentrates of the foregoing, and any combinations thereof.

19. The method of claim 18, wherein the composition further has one or more melanin-uptake-inhibiting agents.

20. The method of claim 18, wherein the one or more melanin-uptake-inhibiting agents is selected from the group consisting of extracts or oils derived from all or parts of the perilla plant, juniperic acid, tomato glycolipid, *Asmunda*

*japonica* Thumb., *stenolama chusana* (L.) ching, *Ligusticum lucidum* Ait, and any combinations thereof.

21. The method of claim 15, wherein said carboxylmethyl cysteamine is present in an amount about 0.001 wt % to about 20 wt % based on the total weight of the composition.

22. A method of lightening skin, hair, lips, and/or nails, comprising: applying topically to an area of the skin, scalp, hair, lips, or nails in need of lightening a composition having
   a) carboxylmethyl cysteamine in a lightening-effective amount;
   b) one or more additional lightening agents; and
   c) a cosmetically acceptable vehicle wherein said one or more additional lightening agents are selected from the group consisting of melanin synthesis regulating agents, melanin uptake-inhibiting agents and combinations thereof.

23. The method of claim 22, wherein the composition is topically applied to treat at least one of the following conditions: freckles, age spots, dark spots on skin, hyperpigmentation, post-inflammatory hyperpigmentation, discoloration of skin, melasma, after-burn scar, nail stain, yellowing of skin, and dark circles under the eye.

24. The method of claim 22, wherein said carboxylmethyl cysteamine is N, N, S (tris) carboxylmethyl cysteamine.

25. The method of claim 22, wherein said carboxylmethyl cysteamine is present in an amount about 0.001 wt % to about 20 wt % based on the total weight of the composition.

26. A method of lightening skin, hair, lips, and/or nails, comprising: applying topically to an area of the skin, scalp, hair, lips, or nails in need of lightening a composition having
   a) carboxylmethyl cysteamine in a lightening-effective amount;
   b) one or more additional lightening agents;
   c) one or more melanin uptake-inhibiting agents; and
   d) a cosmetically acceptable vehicle.

27. The method of claim 26, wherein the composition is topically applied to treat at least one of the following conditions: freckles, age spots, dark spots on skin, hyperpigmentation, post-inflammatory hyperpigmentation, discoloration of skin, melasma, after-burn scar, nail stain, yellowing of skin, and dark circles under the eye.

28. The method of claim 26, wherein said carboxylmethyl cysteamine is N, N, S (tris) carboxylmethyl cysteamine.

29. The method of claim 26, wherein said carboxylmethyl cysteamine is present in an amount about 0.001 wt % to about 20 wt % based on the total weight of the composition.

30. A method of lightening skin, hair, lips, and/or nails, comprising: applying topically to an area of the skin, scalp, hair, lips, and/or nails in need of lightening a composition having
   a) carboxylmethyl cysteamine in a lightening-effective amount;
   b) one or more melanin uptake-inhibiting agents; and
   c) a cosmetically acceptable vehicle.

31. The method of claim 30, wherein the composition is topically applied to treat at least one of the following conditions: freckles, age spots, dark spots on skin, hyperpigmentation, post-inflammatory hyperpigmentation, discoloration of skin, melasma, after-burn scar, nail stain, yellowing of skin, and dark circles under the eye.

32. The method of claim 30, wherein said carboxylmethyl cysteamine is N, N, S (tris) carboxylmethyl cysteamine.

33. The method of claim 30, wherein said carboxylmethyl cysteamine is present in an amount about 0.001 wt % to about 20 wt % based on the total weight of the composition.

* * * * *